United States Patent [19]

Bauerle et al.

[11] 4,095,171
[45] June 13, 1978

[54] ALKALI METAL IONIZATION DETECTOR

[75] Inventors: James E. Bauerle, Plum Borough; William H. Reed, Monroeville; Edgar Berkey, Murrysville, all of Pa.

[73] Assignee: Westinghouse Electric Corp., Pittsburgh, Pa.

[21] Appl. No.: 674,513

[22] Filed: Apr. 7, 1976

[51] Int. Cl.² .................................... G01N 27/00
[52] U.S. Cl. .............................. 324/33; 361/230
[58] Field of Search ......................... 324/33; 317/4; 340/237 R, 237 S; 315/111.9; 313/230; 250/292, 425, 251; 73/40.7, 23, 194 F

[56] References Cited

U.S. PATENT DOCUMENTS

| | | | |
|---|---|---|---|
| 2,742,585 | 4/1956 | Zemany | 324/33 X |
| 3,019,360 | 1/1962 | Hees | 324/33 X |
| 3,244,969 | 4/1966 | Herb et al. | 324/33 |
| 3,416,070 | 10/1968 | McGowan, Jr. | 324/33 |
| 3,439,262 | 4/1969 | Roberts | 324/33 |
| 3,514,655 | 5/1970 | Aria et al. | 324/33 X |
| 3,760,212 | 9/1973 | Mennenga | 324/33 X |
| 3,796,917 | 3/1974 | Hiller | 317/4 |
| 3,808,433 | 4/1974 | Fite et al. | 250/425 X |
| 3,875,499 | 4/1975 | Roberts | 324/33 |

Primary Examiner—Rudolph V. Rolinec
Assistant Examiner—Vincent J. Sunderdick
Attorney, Agent, or Firm—M. P. Lynch

[57] ABSTRACT

Variations in the conventional filament and collector electrodes of an alkali metal ionization detector, including the substitution of helical electrode configurations for either the conventional wire filament or flat plate collector; or, the substitution of a plurality of discrete filament electrodes providing an in situ capability for transferring from an operationally defective filament electrode to a previously unused filament electrode without removing the alkali metal ionization detector from the monitored environment.

In particular, the helical collector arrangement which is coaxially disposed about the filament electrode, i.e. the thermal ionizer, provides an improved collection of positive ions developed by the filament electrode. The helical filament design, on the other hand, provides the advantage of an increased surface area for ionization of alkali metal-bearing species in a monitored gas environment as well as providing a relatively strong electric field for collecting the ions at the collector electrode about which the helical filament electrode is coaxially positioned. Alternatively, both the filament and collector electrodes can be helical.

Furthermore, the operation of the conventional alkali metal ionization detector as a leak detector can be simplified as to cost and complexity, by operating the detector at a reduced collector potential while maintaining the sensitivity of the alkali metal ionization detector adequate for the relatively low concentration of alkali vapor and aerosol typically encountered in leak detection applications.

10 Claims, 11 Drawing Figures

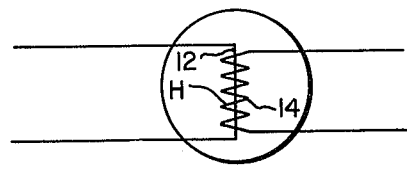 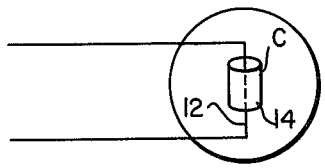
FIG. 2A  FIG. 2B
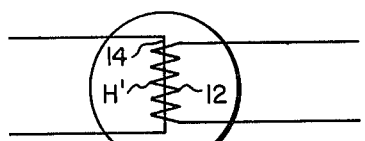 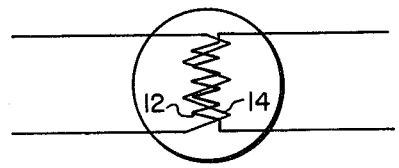
FIG. 2C  FIG. 2D
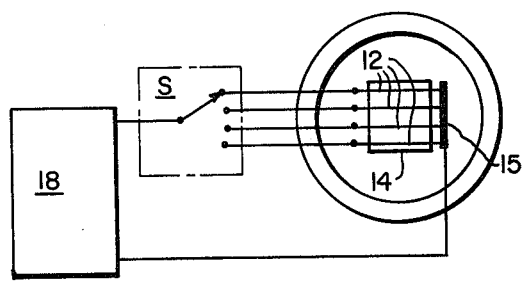 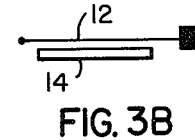
FIG. 3A  FIG. 3B
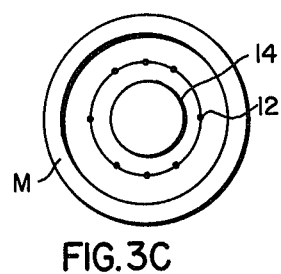 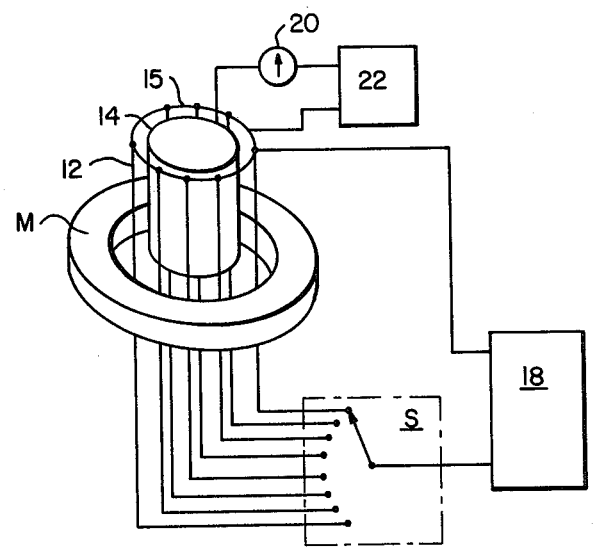
FIG. 3C  FIG. 3D

ALKALI METAL IONIZATION DETECTOR

The invention disclosed herein was made in the course of or under a contract with the United States Energy Research and Development Agency.

BACKGROUND OF THE INVENTION

The basic design concept for an alkali metal ionization detector has been disclosed in numerous prior publications and further has been described in detail in pending U.S. Pat. Applications Ser. No. 435,389 filed Jan. 21, 1974, entitled "A Sensor For Thermally Ionizable Particles And/Or Vapors", and pending U.S. Pat. Application Ser. No. 647,764 filed Jan. 8, 1976, entitled "Improved Filament For Alkali Metal Ionization Detector". Both of the above-identified pending applications are patent applications by the inventors of the subject application and both are assigned to the assignee of the present invention. These pending applications are incorporated herein by reference.

In the prior art type devices, as disclosed in the above-identified pending applications, the alkali metal ionization detector consists of a heated filament electrode also known as a thermal ionizer, and a collector electrode wherein the filament electrode is typically a wire and the collector electrode is a plate. The heated filament electrode thermally ionizes particles of interest in a gas and an electric field is established between the filament electrode and the collector electrode to cause the ions to flow to the collector electrode to produce an ion current which is an indication of the alkali metal concentration of the gas environment to which the heated filament electrode is exposed.

There is disclosed herein modifications to the electrode configuration as well as to the requirements for collector electrode electrical potential which enhance the usefulness of the conventional alkali metal ionization detector as well as minimizing the cost and complexity associated with the conventional implementation of the alkali metal ionization detector.

SUMMARY OF THE INVENTION

There is disclosed herein with reference to the accompanying drawings several techniques for modifying the structure and operation of conventional alkali metal ionization detectors, such as those described in the above-identified pending applications. The substitution of a cylindrical collector configuration, which may take the form of the helical coil, disposed about a straight wire filament electrode, significantly improves the collection efficiency of the collector electrode, while a helical filament design disposed about a straight wire collector electrode significantly increases the surface area at which thermal ionization of alkali metal-bearing species in a gas environment can react to produce positive ions for collection by the collector electrode.

Yet another variation in the electrode configuration disposed herein consists of the use of a plurality of filament electrodes disposed in a symmetrical spatial and geometrical relationship with the collector electrode wherein all but one of the filament electrodes is inactive, with the inactive electrodes serving as backup to the active electrode, and a mechanism for switching between a defective active filament electrode to a previously inactive filament electrode to permit continuing operation of the alkali metal ionization detector without its removal from a monitored environment.

It has been determined experimentally that the conventional operation collector potential of between approximately 90 and 300 volts DC is not required when operating an alkali metal ionization detector, such as a sodium detector as a leak detector wherein the concentration of the alkali metal vapor or aerosol in the monitored gas environment is relatively low. While collector potentials of less than 50 volts DC often produce a limiting ion current condition, or space charge limited current condition, in the presence of relatively high concentrations of an alkali metal vapor or aerosol, this restriction is of little consequence when operating the alkali metal ionization detector as a leak detector in relatively low concentrations of alkali metal atoms.

The selection of a relatively low operating collector potential for an alkali metal ionization detector functioning as a leak detector is based on the selection of a value of the collector potential which is high enough to avoid ion-electron recombinations and to avoid background interference effects from masking signal, as well as high enough to avoid space charge limited ion flow over the desired concentration range for leak detection applications.

BRIEF DESCRIPTION OF THE DRAWINGS

The invention will become more readily apparent from the following exemplary description in connection with the accompanying drawings:

FIGS. 2A, 2B, 2C, and 2D; 3A, 3B, 3C and 3D are schematic illustrations of alternate electrode configurations suitable for substitution in the embodiment of FIG. 1.

DESCRIPTION OF THE PREFERRED EMBODIMENT

Figure 1:
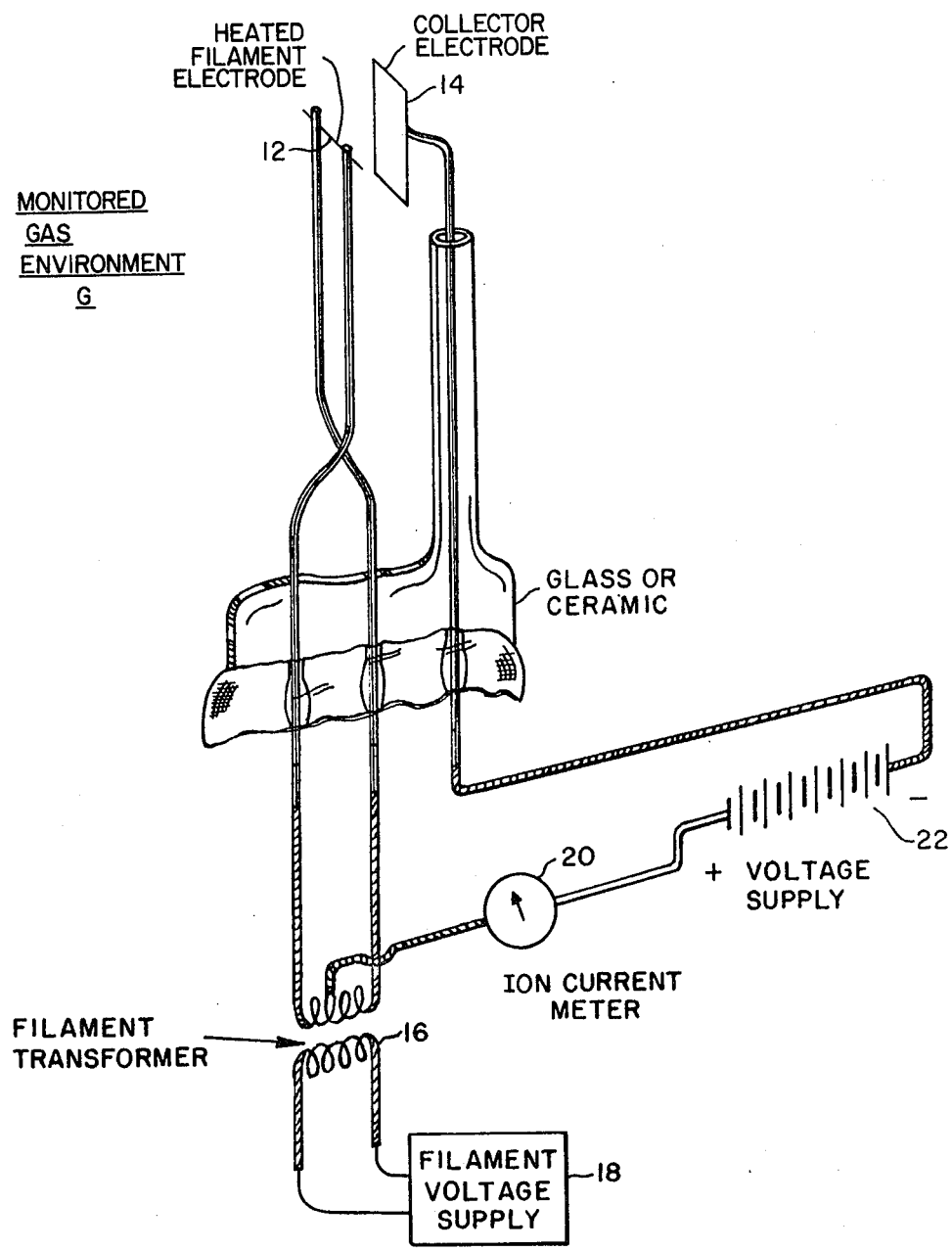
FIG. 1 is a schematic illustration of a conventional alkali metal ionization detector.

The alkali metal ionization detector, as typically illustrated in FIG. 1, employs a heated filament electrode 12, or thermal ionizer electrode, which responds to impinging alkali metal atoms or alkali metal-containing compounds, i.e. vapor or aerosol, to form positive alkali metal ions which are attracted to a collector electrode 14 via an electric field to produce an ion current which is an indication of the alkali metal concentration of the monitored gas environment G to which the heated filament electrode 12 is exposed. The filament transformer 16 couples filament voltage from filament voltage supply 18 to heat the filament electrode 12. The ion current meter 20 provides an indication of the ion current flow established between the heated filament electrode 12 and the collector electrode 14 by the electric field developed between the heated filament electrode 12 and the collector electrode 14 by the collector potential of the collector voltage supply 22.

Alkali metal-containing particles, whether in the form of a vapor, aerosol, or compound, transported by a carrier gas present in the monitored gas environment G to the vicinity of the detector 10, are converted to free alkali metal ions at the surface of the heated filament electrode 12 which functions as a thermal ionizer. These ions are then collected by the collector electrode 14 which is maintained at a negative collector potential relative to the heated filament electrode 12 by the collector voltage supply 22. The flow of ions thus established produces an ion current which is measured by the ion current meter 20 as an indication of the concentration of the alkali metal present in the monitored gas environment G adjacent to the heated filament electrode 12. The process by which the alkali metal-containing particles are converted to free alkali metal ions can be thought of as occurring in the following steps: (1) the collision of the alkali metal-containing particles with the surface of the heated filament electrode 12 and their subsequent melting; (2) the rapid surface diffusion (and in the case of compounds, dissociation) of the melted alkali metal-containing particles over the heated filament electrode 12 to form a layer of adsorbed alkali metal atoms; (3) the transfer of valence electrons from some of the adsorbed alkali metal atoms to the heated filament electrode 12, converting them to adsorbed alkali metal ions; and, (4) the description of the alkali metal ions from the surface to become free ions, as well as the desorption of neutral alkali metal ions. The free alkali metal ions thus generated contribute to the ion current monitored by the ion current meter 20.

Traditional heated filament materials include platinum, platinum-rhodium, tungsten, etc. while alkali metal ionization detectors recently developed for use in oxygen environment are disclosed in the above-referenced pending application, Ser. No. 647,464 as achieving improved operating effectiveness through the use of conventional furnace heating element material such as nichrome, Kanthal A, and Super Kanthal. In the latter materials an oxide coating is formed on the heated filament electrode to increase the operational life of the heated electrode. Suitable collector electrode materials include molybdenum, nickel, stainless steel, etc.

ALTERNATE ELECTRODE CONFIGURATIONS

The electrode configurations illustrated schematically in FIGS. 2A, 2B, 2C and 2D represent coaxial arrangements of the heated filament electrode and the collector electrode while the electrode configurations illustrated in FIGS. 3A, 3B and 3C represent embodiments utilizing multiple filament electrodes in combination with a common collector electrode.

The embodiment of FIG. 2A consists of a helical coil collector electrode 14 wound in a cylindrical relationship about a straight wire or ribbon filament electrode 12. The prime advantage of the embodiment of FIG. 2A results from the substantial collection efficiency of the helical coil collector electrode 14 in responding to the positive ions leaving the filament electrode 12 because of the cylindrical nature of the helical coil collector electrode 14. Further, the helical configuration of the collector electrode 14 offers little or no restriction to the flow of the gas in the monitored gas environment G into a contacting relationship with the heated filament electrode 12. The collector electrode 14 is maintained at a negative potential with respect to the filament electrode 12 by the collector voltage supply 22. The electric field developed in the region between the filament electrode 12 and the collector electrode 14 is effective in directing the positive ions emitted from the filament electrode 12 to the helix H of the collector electrode 14.

In the embodiment of FIG. 2B, the collector electrode 14 consists of an open-ended cylinder element C coaxially disposed about a straight wire or ribbon filament electrode 12. The open-ended cylinder element C provides essentially 100% collection efficiency with substantially all positive ions emitted by the filament electrode 12 being collected by the open-ended cylinder element C of the collector electrode 14. In the event the open-ended cylinder element C represents an undesirable restriction of the movement of gas into contact with the filament electrode 12, the combination of the open-ended cylindrical element C and the filament electrode 12 can be positioned within the monitored gas environment G such that gas flow occurs parallel to the longitudinal axis of the open-ended cylinder element C. Further, while it is not shown, a separate gas flow means can be incorporated in combination with the alkali metal ionization detector 10 to establish a flow of the gas in the monitored gas environment in a direction parallel to the longitudinal axis of the open-ended cylinder element C. The gas flow concern can also be satisfied by using a mesh or porous material for the cylinder element C.

In the embodiment of FIG. 2C, the filament electrode 12 is in the form of a helix H' disposed about a straight wire or ribbon collector electrode 14. The most significant advantage of this electrode configuration is the increased surface area for ionization of alkali metal-bearing species in the monitored gas environment G afforded the filament electrode 12. Further, the arrangement of a coaxial filament electrode about a centrally positioned collector electrode supports the development of a strong electric field for the collection of positive ions at the centrally disposed collector electrode.

The embodiment of FIG. 2D illustrates a coaxial arrangement of helix electrode configurations for both the filament electrode 12 and the collector electrode 14.

The electrode configuration of FIGS. 3A, 3B and 3C illustrates the use of a plurality of filament electrodes 12 in combination with a single collector electrode 14 wherein one of the filament electrodes 12 is used as the active filament electrode of the alkali metal ionization detector 10 with the additional filament electrodes functioning as auxiliary or backup electrodes available for substitution for the active electrode in the event of a failure of the active electrode. This redundancy eliminates the need for removing the alkali metal ionization detector 10 from the monitored gas environment G in the event of failure of a filament electrode. This feature is particularly desirable in nuclear applications. Furthermore, the availability of auxiliary filament electrodes and a suitable means for selecting one of the filament electrodes as the active electrode, provides an in situ capability for checking the operational integrity of the active filament electrode as well as affording calibration capabilities.

The embodiment illustrated in FIGS. 3A and 3B consists of a flat plate collector electrode 14 having a plurality of straight wire filament electrodes 12 positioned equally distant from the flat plate collector electrode 14 and forming a plane parallel to the flat plate collector electrode 14. The straight wire filament electrodes 12 are connected in common at one end while the opposite ends are coupled through a selector switch S to the filament voltage supply 18.

The collector supply voltage 22 is connected between the flat plate collector electrode 14 and the filament electrode common 15 to develop the electric field between filament electrode 12 and the collector electrode 14 as described above.

In order for the operation of the alkali metal ionization detector 10 to be consistent regardless of which of the plurality of filament electrodes 12 of the embodiment of FIGS. 3A, 3B, 3C and 3D is functioning as the active filament electrode, each of the filament electrodes must be maintained at a substantially identical spatial and geometrical relationship with respect to the collector electrode. Failure to maintain this spatial and geometrical relationship may produce an uncertainty in the interpretation of the ion current measured by the ion current meter 20. Obviously, in this applications where exact operation equivalency between each of the filament electrodes of a multi-filament electrode configuration, is not essential, then slight variations in the spatial and geometrical relationship of the filament electrodes 12 with respect to the collector electrode 14 may be tolerated.

In the embodiments of FIGS. 3C and 3D, the common collector electrode 14 takes the form of a cylinder about which a plurality of straight wire filament electrodes 12 are disposed to define a cylinder coaxially positioned about the cylindrical collector electrode 14. As in the embodiment of FIGS. 3A and 3B, one end of each of the filament electrodes 12 is connected to a filament common 15 while the opposite ends are coupled through a selector switch S to the filament supply voltage source 18. A sensor mounting M is illustrated for maintaining the cylindrical arrangement of the plurality of filament electrodes 12 in a coaxial configuration about the cylindrical collector electrode 14. The collector supply voltage 22 is connected between the collector electrode 14 and the filament common 15. The identical spatial and geometric positioning of each of the filament electrodes 12 with respect to the cylindrical collector electrode 14 provides essentially identical alkali metal ionization detector operation regardless of which of the filament electrodes 12 is selected to be the active electrode by the selector switch S.

LOW VOLTAGE MODE OF OPERATION OF AN ALKALI METAL IONIZATION DETECTOR

Conventional thermal ionization type instruments have been designed to detect the presence of easily ionizable species in a carrier gas and have employed relatively high voltages between the heated filament electrode and the collector electrode. These voltages have typically ranged from 90 volts to 300 volts DC. The value of the voltage employed, or more properly the magnitude of the electric field developed between the filament and collector electrodes, has a marked effect on the behavior of the ions in the gap, or spacing, between the electrodes. At sufficiently low voltages, and correspondingly low electric fields, the ions and electrons can recombine after being formed due to the longer transit times between the filament and collector electrodes and thus the magnitude of the ion current is less than that which would be realized at higher collector voltage operation. A further limitation encountered when using voltages less than that described with respect to conventional thermal ionization type instruments, is that the ion current can become space charged limited, assuming that there is sufficient signal generating species available, resulting in less than the maximum possible current being collected.

Theoretically, a low collector potential can be defined as one for which the electric field between the filament and collector electrodes is low. In the theory of ion mobility, an electric field is considered to be low, medium, or high corresponding to whether the energy ($W_{field}$) gained by the ions from the electric field on each free path (between collisions) is much less than, equal to, or much greater than the thermal energy ($W_{thermal}$) of the ions. Symbolically, the condition for low field is given by:

$$W_{field} << W_{thermal} \qquad (1)$$

It can be shown that $$W_{thermal} \cong kT \qquad (2)$$

and $$W_{field} \cong e\lambda\epsilon \qquad (3)$$

where $k$ is Boltzmann's constant, T = absolute temperature of the gas, $e$ is the ionic charge, $\lambda$ is the ion mean free path and $\epsilon$ is the electric field. For an alkali metal ionization detector in which the straight wire filament-flat plate collector geometry of FIG. 1 is employed, it can be shown that the electric field near the filament is given approximately by:

$$\epsilon \cong \frac{V_o}{r_1 \ln \frac{r_2}{r_1}} \qquad (4)$$

where $V_o$ is the collector potential, $r_1$ is the filament radius and $r_2$ is the filament-to-collector distance. Combining equations (1), (2), (3), and (4) one obtains the condition for low collector potential, $$V_o << \frac{kTr_1}{\lambda e} \ln \frac{r_2}{r_1} \qquad (5)$$
$$V_o << 140 \text{ volts}$$

for a collector potential to be considered low. It is reasonable then to list low, medium, and high collector potentials as follows:

$V_o \leq 47$ volts (low)

$V_o \approx 140$ volts (medium)

$V_o \geq 420$ volts (high)

Reference: *Theory of Gaseous Conduction and Electronics*, chapter 7, by F. A. Maxfield and R. R. Benedict, McGraw-Hill, 1941.

Practically, a low collector potential can be defined as one for which the saturation (space charge-limited) current is no greater than 100 times the background ion current. For a typical alkali metal ionization detector operating in room atmosphere the background current might be as high as 0.1nA, so that the upper current limit for low voltage operation would be about 10nA, implying a collector potential on the order of 20 volts or less.

It has been determined experimentally, that applications of conventional thermal ionization type alkali metal ionization detector, as illustrated in FIG. 1, as leak detectors wherein the detectors are required to sense very low concentrations of alkali metal species, the above-identified problems associated with low collector operating potentials are relatively unimportant. The use of low collector electrode operating voltage of between 50 volts DC, in place of the conventional voltage of between 90 and 300 volts DC, significantly simplifies the electronics package associated with the alkali metal ionization detector.

It has been determined experimentally, that for optimum sensitivity of the alkali metal ionization detector as a leak detector, the magnitude of the collector voltage provided by collector supply voltage source 22 corresponds to a magnitude sufficiently high to avoid ion-electron recombinations, avoid background interference effects from masking the ion current measured by ion current meter 20, and sufficiently high to avoid space charge limited ion flow over the desired concentration range to be detected.

Figure 4A:
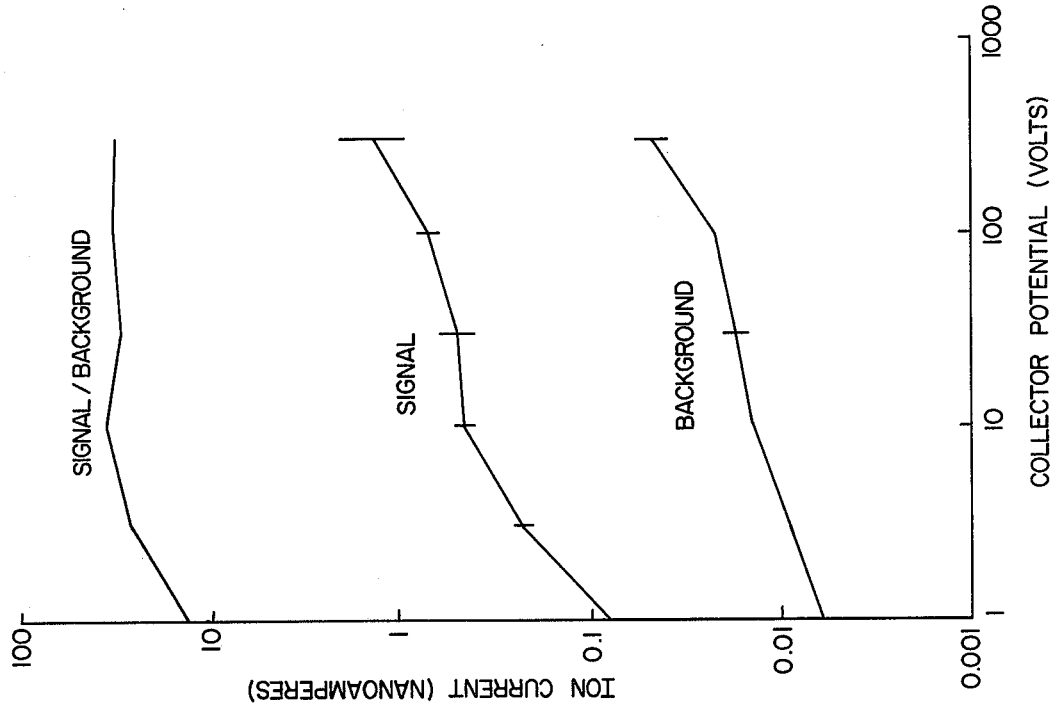
FIGS. 4A and 4B are graphical illustrations of the operation of the alkali metal ionization detector of FIG. 1 at collector electrode potentials lower than the collector potentials employed in prior art alkali metal ionization detectors.

Referring to the experimental data represented in the graph of FIG. 4A, it is apparent that the limiting ion current is approximately 350 nanoamperes at a collector electrode voltage of 90 volts, while it is only approximately 10 nanoamperes at a collector electrode voltage of 15 volts. While the data represented in FIG. 4A corresponds to information derived from the operation of an alkali metal ionization detector designed for monitoring sodium ions, the operational conclusions apparent from FIGS. 4A and 4B apply equally to thermal ionizer type alkali metal ionization detectors in general.

The low end of the detection range of the alkali metal ionization detector represented by the graphical information of FIG. 4A, covers a sodium concentration range of approximately $3 \times 10^{-12}$ to $3 \times 10^{-9}$ gmNa/cc of gas, which corresponds to ion currents of approximately 0.01 to 10 nanoamperes. It is apparent therefore that the ion current developed while operating in the low concentration regime at a conventional collector potential of 90 volts, is well below the limiting value. Consequently, it is possible to lower the collector electrode potential and still retain the operating characteristics of the alkali metal ionization detector providing the detector is restricted to operating over a low alkali metal concentration range, such as that encountered in leak detection operation. For example, by lowering the collector electrode potential to 15 volts, it is possible to avoid space charge limited flow over the entire sodium concentration range cited above. The maximum ion current will be about 10 nanoamperes, which is approximately at the limiting value.

Therefore, it is apparent, that if the primary function of the alkali metal ionization detector is that of a leak detector, collector electrode potentials of less than 50 volts DC, and in particular in the range of 10 to 20 volts DC, are quite satisfactory and will produce no change in the operating mode of the alkali metal ionization detector. The capability of operating at the low collector electrode potentials, as cited above, eliminates the requirements for high voltage components and the accompanying cost and safety drawbacks. Miniaturization of the alkali metal ionization detector and associated electronics is further possible inasmuch as the power supply typically used with electronics and the readout circuitry associated with the ion current meter 20 can function also as a collector electrode voltage supply 22.

Figure 4B:
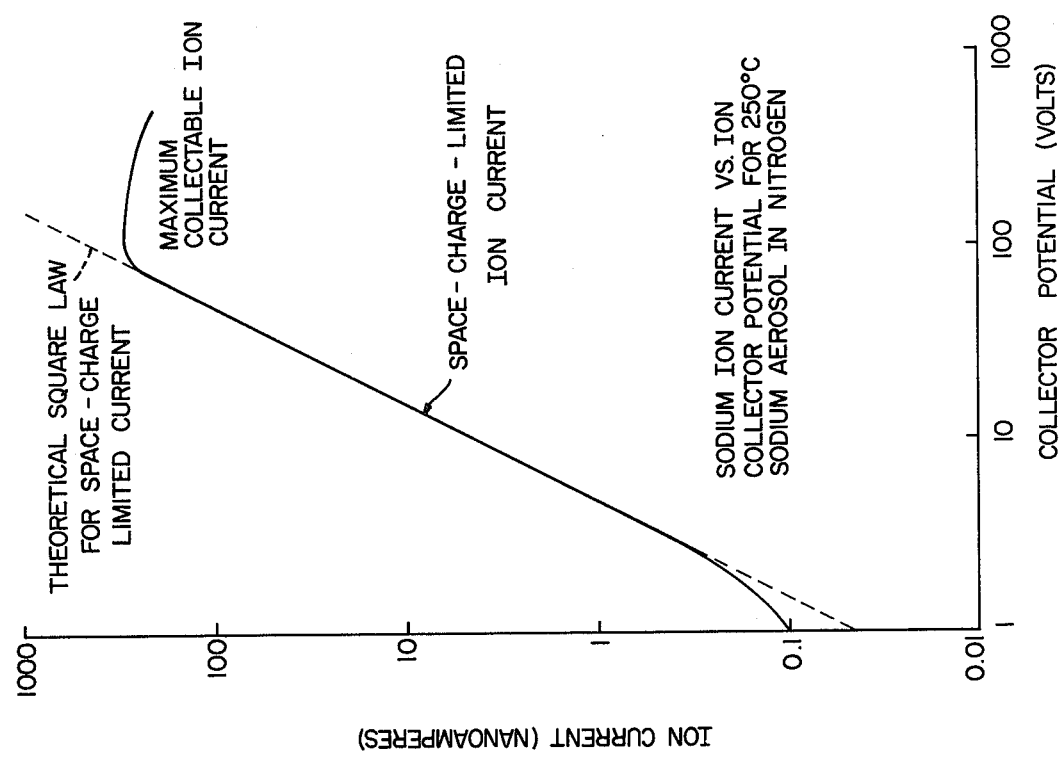

The graphical information illustrated in FIG. 4B provides experimental verification that the performance of the alkali metal ionization detector is not degraded by reducing the collector operating potential as described above. The ion current signal response of the alkali metal ionization detector is measured as a function of the collector electrode potential while the sodium vapor, aerosol concentration is held constant. Both the measured ion current signal and the background effect decreases with decreasing collector electrode potential, and it is important to note that the signal-to-background ratio remains approximately constant over a wide range of collector electrode potential. The signal-to-background ratio only begins to decrease at collector electrode potentials of less than 10 volts. This decrease indicates a gradual transition to a space charge limited condition. The minimum required collector electrode potential to avoid the space charge limited condition can be determined on the basis of filament electrode to collector electrode spacing, the alkali metal ion mobility, and a value for maximum ion current to be measured for a leak detection application of the alkali metal ionization detector, i.e. 1 to 10 nanoamperes.

While there is a slight decrease in the background ion current with decreasing collector electrode potential, which can be attributed to an increase in ion recombination resulting from longer ion transit times at lower voltages, the constant signal-to-background ratio confirms that there is essentially no loss in sensitivity if the alkali metal ionization detector is operated as a leak detector at low collector electrode potentials.

We claim:

1. In an alkali metal ionization detector having a heated filament electrode for thermally ionizing alkali metal atoms or alkali metal-containing particles in a monitored gas environment to form positive ions and a source of electrical potential connected to a collector electrode to attract the positive ions and establish an ion current flow which is indicative of the concentration of the alkali metal atoms or alkali metal-containing particles, the combination of an electrode arrangement comprising a single collector electrode and a plurality of heated filament electrodes adapted to be selectively activated in combination with the collector electrode to develop said ion current flow, only one of said heated filament electrodes being activated in combination with the collector electrode at any given time, said plurality of filament electrodes being disposed with respect to said collector electrode such that the ion current flow in response to the monitored gas environment is substantially identical regardless of which of the filament electrodes is selectively activated for operational combination with said collector electrode.

2. An alkali metal ionization detector as claimed in claim 1 including means for selectively activating one of said plurality of heated filament electrodes for operational combination with said collector electrode to produce said ion current flow as an indication of the alkali metal concentration of a monitored gas environment.

3. In an alkali metal ionization detector as claimed in claim 1 wherein said collector electrode is a flat electrode element.

4. In an alkali metal ionization detector as claimed in claim 1 wherein said collector electrode is an open-ended cylinder.

5. An alkali metal ionization detector as claimed in claim 2 wherein one end of each of said plurality of heated filament electrodes is connected in common, while the opposite end of each of said plurality of heated filament electrodes is connected to said means for selectively activating the heated filament electrodes.

6. An alkali metal ionization detector as claimed in claim 4 wherein each of said plurality of heated filament electrodes is a straight wire electrode element in spaced-apart parallel relationship with respect to each other and disposed about said cylinder electrode to form a cylindrical arrangement of said plurality of heated filament electrodes coaxially disposed about said collector electrode.

7. A method for operating an alkali metal ionization detector as a leak detector wherein the collector potential establishes an electric field between a heated filament electrode, which functions as a thermal ionizer to produce positive ions in response to impinging alkali metal atoms or alkali metal-containing particles, and a collector electrode, to establish ion flow between said heated filament electrode and said collector electrode, the ion current flow thus established being indicative of the alkali metal atom or particle concentration of the environment to which the heated filament electrode is exposed, comprising the step of, adjusting the magnitude of the collector potential slightly above the collector potential magnitude at which the ion flow from the heated filament electrode to the collector electrode is subject to space charge limited conditions.

8. In a method as claimed in claim 7 wherein said collector potential is adjusted to support ion current flow in a range of about 1 to 10 nanoamperes.

9. In an alkali metal ionization detector for thermally ionizing alkali metal atoms or alkali metal-containing particles in a monitored gas environment to form positive ions and develop an ion current flow between electrodes which is indicative of the concentration of the alkali metal atoms or the alkali metal-containing particles, the combination of, an electrode arrangement comprising a first and second electrode, said first electrode being a straight heated filament electrode, and said second electrode being a helical collector electrode wound about said heated filament electrode, said heated filament electrodes operating to thermally ionize alkali metal atoms or particles contacting said heated filament electrode to produce positive ions, and electrical potential means for developing electrical potential between said first and second electrodes to establish ion flow from said heated filament electrode to said helical collector electrode.

10. In an alkali metal ionization detector for thermally ionizing alkali metal atoms or alkali metal-containing particles in a monitor gas environment to form positive ions and develop an ion current flow between electrodes which is indicative of the concentration of the alkali metal atoms or the alkali metal-containing particles, the combination of, an electrode arrangement comprising a first and second electrode, said first electrode being a straight collector electrode, and said second electrode being a heated helical filament electrode disposed about said collector electrode, said heated helical filament electrode thermally ionizing alkali metal atoms or particles contacting said heated helical filament electrode to form positive ions, an electrical potential means for developing an electrical potential between said first and second electrodes to establish ion flow from said heated helical filament electrode to said collector electrode.

* * * * *